United States Patent [19]

Rogers

[11] Patent Number: 4,468,448

[45] Date of Patent: Aug. 28, 1984

[54] PHOTOGRAPHIC PRODUCTS AND PROCESSES

[75] Inventor: Howard G. Rogers, Weston, Mass.

[73] Assignee: Polaroid Corporation, Cambridge, Mass.

[21] Appl. No.: 500,366

[22] Filed: Jun. 2, 1983

[51] Int. Cl.³ .......................... G03C 1/40; G03C 7/00; G03C 5/54

[52] U.S. Cl. .................................... 430/222; 430/241; 430/375; 430/542; 430/559

[58] Field of Search .............. 430/222, 559, 542, 375, 430/241

[56] References Cited

U.S. PATENT DOCUMENTS

| | | | |
|---|---|---|---|
| 3,443,941 | 5/1969 | Rogers | 430/222 |
| 3,719,489 | 3/1973 | Cieciuch et al. | 430/222 |
| 4,060,417 | 11/1977 | Cieciuch et al. | 430/222 |
| 4,248,962 | 2/1981 | Lau | 430/559 |
| 4,358,525 | 11/1982 | Mooberry et al. | 430/222 |

*Primary Examiner*—Richard L. Schilling
*Attorney, Agent, or Firm*—Sybil A. Campbell

[57] ABSTRACT

This invention relates to photographic processes and products for forming an image in dye from a colorless precursor of a preformed image dye which is substituted with a moiety comprising a 1,3-sulfur-nitrogen group that undergoes cleavage in the presence of silver ion and/or soluble silver complex, which moiety maintains said precursor in its colorless form at least until the 1,3-sulfur-nitrogen group undergoes cleavage imagewise to correspond to the imagewise distribution of silver ion and/or soluble silver complex made available as a function of development.

18 Claims, No Drawings

PHOTOGRAPHIC PRODUCTS AND PROCESSES

BACKGROUND OF THE INVENTION

1. Field of the Invention

This invention relates to the formation of dye images from a substantially colorless precursor of a preformed image dye. In another aspect, this invention relates to photographic products and processes for providing an imagewise distribution of a reagent such as a photographically active reagent or an image dye-providing moiety and to novel compounds useful therein.

2. Description of the Prior Art

U.S. Pat. No. 3,719,489 describes and claims photographic processes employing initially photographically inert compounds which are capable of undergoing cleavage in the presence of the imagewise distribution of silver ions made available during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Compounds disclosed as useful in liberating a reagent in the presence of said silver ions and/or silver complex are sulfur-nitrogen compounds containing the group

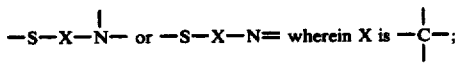

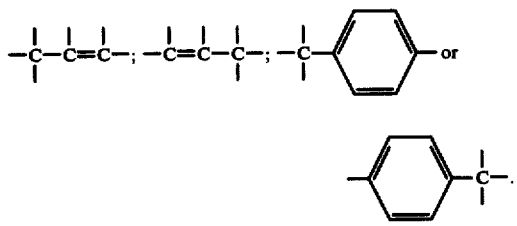

These 1,3-sulfur-nitrogen compounds may be linear or cyclic in structure, and in a particularly preferred embodiment are cyclic compounds, such as, thiazolidine compounds which comprise a dye radical having the chromophoric system of an azo, anthraquinone, phthalocyanine or other dye and a thiazolidin-2'-yl moiety which may be bonded directly to the dye radical or indirectly through an appropriate linking group.

The present invention is concerned with another method of forming a color image.

SUMMARY OF THE INVENTION

According to the present invention, the ability of 1,3-sulfur-nitrogen compounds to undergo silver ion assisted cleavage in an imagewise fashion is utilized to provide an imagewise distribution of a colored image dye from a substantially colorless precursor of a preformed image dye by employing a moiety comprising a 1,3-sulfur-nitrogen group to maintain said precursor in its substantially colorless form until said 1,3-sulfur-nitrogen group undergoes cleavage imagewise to correspond to the imagewise distribution of silver ion and/or soluble silver complex formed as a function of development of an imagewise exposed photosensitive element.

It is, therefore, the primary object of the present invention to provide photographic products and processes for forming a dye image from a colorless precursor of a preformed image dye which is substituted with a moiety comprising a 1,3-sulfur-nitrogen group that undergoes cleavage in the presence of silver ion and/or soluble silver complex, which moiety maintains said precursor in its colorless form at least until the 1,3-sulfur-nitrogen group undergoes cleavage imagewise to correspond to the imagewise distribution of silver ion and/or soluble silver complex made available as a function of development.

Other objects of the invention will in part be obvious and will in part appear hereinafter.

The invention accordingly comprises the processes involving the several steps and the relation and order of one or more of such steps with respect to each of the others, and the product and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

The present invention is concerned with a photographic color process which provides a dye image, said process comprising photoexposing a photosensitive element containing a silver halide emulsion, said silver halide emulsion having associated therewith a colorless precursor of a preformed image dye; developing said exposed silver halide emulsion to form an image in developed silver and an imagewise distribution of silver ion and/or soluble silver complex in the partially developed and undeveloped areas of said emulsion; and forming as a function of said development a color image in dye from said colorless precursor, said colorless precursor of a preformed image dye being substituted with a moiety comprising a 1,3-sulfur-nitrogen group, which moiety maintains said precursor in its colorless form at least until said 1,3-sulfur-nitrogen group undergoes cleavage in the presence of said silver ion and/or soluble silver complex formed as a function of development. Preferably, the silver halide emulsion is a negative working emulsion and the color image is a positive image in dye.

The colorless image dye-providing compounds that may be employed in the above process may be represented by the formula (I) M—Z wherein M is a moiety comprising a 1,3-sulfur-nitrogen group that undergoes cleavage in the presence of silver ions and/or soluble silver complex and Z is the radical of a colorless precursor of a preformed image dye, said moiety being substituted on said precursor such that the precursor is maintained in its colorless form at least until said 1,3-sulfur-nitrogen group undergoes cleavage.

The color image may be formed by using the imagewise cleavage of the 1,3-sulfur-nitrogen group to provide the image dye directly, or the imagewise cleavage of the 1,3-sulfur-nitrogen group may be used to activate a subsequent reaction or series of reactions which in turn provides the image dye. The silver ion assisted cleavage reaction together with any subsequent reaction or series of reactions should, of course, provide the image dye at a photographically useful rate in a given photographic system.

The 1,3-sulfur-nitrogen group may be derived from the various compounds disclosed in aforementioned U.S. Pat. No. 3,719,489 including both the linear and cyclic compounds containing the grouping —S—X—N or —S—X—N= wherein X is

Particularly preferred are the cyclic compounds where both the S and N atoms are included in the ring and especially the cyclic compounds illustrated in the following formula

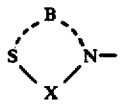

wherein B represents the atoms, preferably carbon atoms, necessary to complete a ring system containing at least 4 members and usually up to 20 members and X is

Examples of such compounds include thiazolidines, benzothiazolines and 1,2-tetrahydrothiazines.

As an illustration of providing the image dye by a reaction subsequent to said cleavage reaction, the moiety M may comprise a 1,3-sulfur-nitrogen group substituted in the 2-position with an amide moiety that undergoes an intramolecularly accelerated cleavage reaction as a result of the cleavage of said 1,3-sulfur-nitrogen group. As an illustration, a thiazolidinyl group may be used to mask the α-keto group of an α-ketoamide, such as, a glyoxalamide to depress its hydrolysis rate and provide a masked compound that is substantially stable to alkaline hydrolysis until the 1,3-sulfur-nitrogen group undergoes cleavage in the presence of silver ion and/or soluble silver complex. A 1,3-sulfur-nitrogen group also may be used to mask the aldehyde group of a phthalaldehydamide to prevent the aldehyde group from assisting the hydrolysis of the neighboring carboxamido group until such time as the 1,3-sulfur-nitrogen group undergoes said silver ion assisted cleavage. Examples of colorless precursors of preformed image dyes employing glyoxalamides and phthalaldehydamides masked by a 1,3-sulfur-nitrogen group, viz., a thiazoidinyl group are set out below

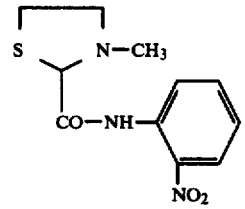

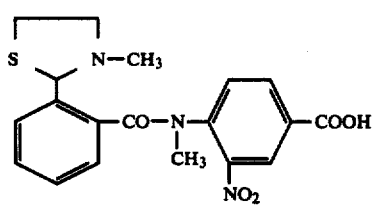

wherein the image dyes provided are the nitroaniline dyes,

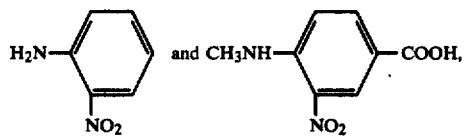

respectively. The formation of dye images from colorless precursors such as compounds (1) and (2) that undergo an intramolecularly accelerated amide cleavage reaction following the imagewise cleavage of a thiazolidinyl group form the subject matter of copending U.S. patent application Ser. No. 500,415 of James W. Foley filed concurrently herewith.

As a further illustration of providing the image dye by a reaction activated by said imagewise cleavage, the moiety M may comprise a 1,3-sulfur-nitrogen group possessing a substituent in the 2-position that undergoes a β-elimination reaction following the cleavage of said thiazolidinyl group. β-elimination reactions are well known in the art and involve the breaking of bonds, for example, a C—N, C—O, C—S, C—Se, N—N, N—O or other bond to release a leaving group, which in this instance would comprise the image dye. The rate constants for various leaving groups in elimination reactions β-substituted sulphones, β-substituted phenyl ketones and β-substituted esters have been reported by Charles J. M. Stirling et al, J. Chem. Soc. (B), 1970, pages 672 and 684; Charles J. M. Stirling et al, J. Chem. Soc. Chem. Commun., page 941 (1975); and Charles J. M. Stirling, Acc. Chem. Res. 12, pages 198–203 (1979). Some model leaving groups from a carbon system that may be derivatized to provide the desired image dye-providing compounds include —SMe; —SPh; —SePh; —OPh; —OMe; —P(O)(OEt)$_2$; —NHTs; —C(Me)$_2$NO$_2$; —N(Me)Ts; —N(Me)Ac; —N(Ph)Ac; —N(Ph)Ts; —N(Ph)CO$_2$CH$_2$Ph and —N(Me)CO$_2$Ph wherein Me, Et, Ph, Ac and Ts represent methyl, ethyl, phenyl, acetyl and tosyl, respectively.

Also, the β-elimination reaction may be one of a series of reactions to release the image dye. For example, the β-elimination reaction following the cleavage of a thiazolidinyl group may be used to generate a moiety capable of undergoing an intramolecularly accelerated nucleophilic displacement reaction, which nucleophilic displacement reaction, in turn, provides the imagewise distribution of dye. Examples of colorless precursors of preformed image dyes employing a β-elimination reaction for providing the dye image are set out below

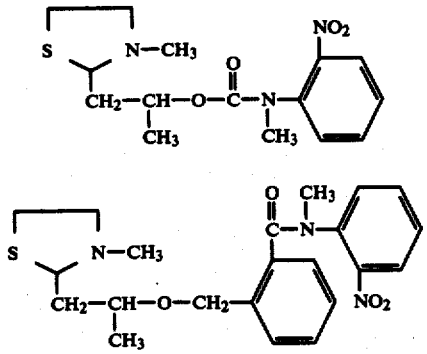

wherein the image dye released is the nitroaniline dye,

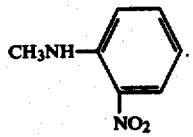

The formation of dye images from colorless precursors such as compound (3) that undergo a β-elimination reaction following the imagewise cleavage of a thiazolidinyl group form the subject matter of copending U.S. Patent Application Ser. No. 500,391 of Roberta R. Arbree, James W. Foley and Frank A. Meneghini filed concurrently herewith. The formation of dye images from colorless precursors such as compound (4), which subsequent to the imagewise cleavage of a thiazolidinyl group, undergo a β-elimination reaction followed by an intramolecularly accelerated nucleophilic displacement reaction forms the subject matter of copending U.S. Patent Application Ser. No. 500,414 of Frank A. Meneghini and Paul S. Palumbo also filed concurrently herewith.

The image dye released from the colorless precursor compounds may comprise any of the general classes of dyes known in the art, for example, nitro, azo, xanthene and anthraquinone dyes; also leuco, indicator, temporarily "color shifted" and other dyes that take on a color change during or subsequent to processing to provide the ultimately desired color for the dye image via oxidation, changes in pH, alkaline hydrolysis of a blocking group, etc. It will be appreciated that in the present invention such a color change is precluded without removal of the moiety, M, and also that said moiety and/or the radical of the colorless precursor of the preformed image dye may be substituted with solubilizing, ballasting or other groups as may be appropriate for a given photographic process.

The following examples are given to further illustrate the present invention and are not intended to be limiting.

EXAMPLE 1

Preparation of the compound having the formula

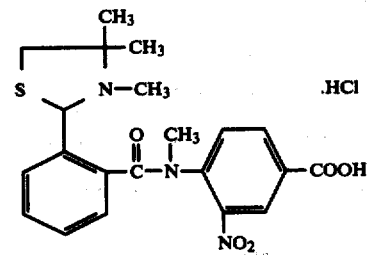

2-(2'-carboxyphenyl)-3,5,5-trimethyl-thiazolidine (6.00 g; 0.0239 mol) was mixed with 1,1'-carbonyldiimidazole (3.88 g; 0.0239 mol) in 70 mls of dry N,N-dimethylformamide (DMF). Carbon dioxide evolution was observed. After stirring for one hour at room temperature, 4-carboxy-2-nitro-N-methylaniline (4.69 g; 0.0239 mol) was added providing an orange solution. Portion-wise addition of sodium hydroxide (50% oil dispersion, 3.44 g; 0.0717 mol) over a twenty minute period was accompanied by hydrogen evolution and an exotherm (to 50° C.). The resulting dark brown slurry was stirred at ambient temperature for fifteen minutes producing a dark brown gel. The mixture was kept overnight in the dark and under nitrogen. The mixture was acidified with dilute hydrochloric acid (14 ml conc. HCl in 130 ml of water), then adjusted to pH 4 with dilute aqueous sodium hydroxide. The mixture was filtered to give 2.7 g of an orange-yellow solid (the 2-nitro-4-carboxy-N-methylaniline reactant). The aqueous-DMF filtrate was saturated with sodium chloride and extracted with chloroform. A solid appeared (insoluble in both layers) which was filtered, washed with water and acetone. After drying, 1.96 g of the title compound was obtained as a cream powder; melting range 251.5°–253.5° C. (dec.). The dried (sodium sulfate) chloroform layer was evaporated to provide an orange oil which was triturated with 100 ml of ether. Solid appeared and was filtered off (1.57 g of the starting thiazolidine reactant). The ether filtrate was treated with HCl gas to precipitate 2.24 g of the mixed hydrochlorides of the starting thiazolidine reactant and of the title compound. Separation was achieved by dissolving the mixture in 15 ml of boiling methanol. After carbon treatment and filtration, ether (100 ml) was added to the methanolic solution along with some seed crystals of the title compound. In this manner an additional 0.81 g of the title compound was realized; melting point 255° C. (dec.); total yield 2.77 g (25% by weight).

Analysis for $C_2$, $H_{24}ClN_3O_5S$: Calculated: C, 54.1; H, 5.2; Cl, 7.6; N, 9.0; O, 17.2; S, 6.9; Found: C, 54.0; H, 5.3; Cl, 7.7; N, 8.9; O, 17.4; S, 6.7.

EXAMPLE 2

Preparation of the compound having the formula

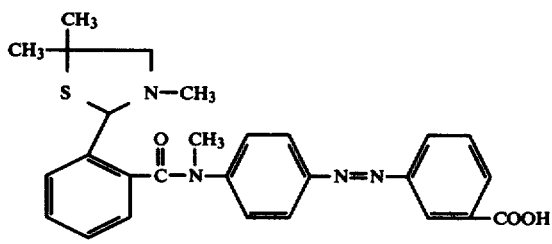

2.51 g of 2-(2'-carboxyphenyl)-3,5,5-trimethyl-thiazolidine and 1.62 g of 1,1'-carbonyldiimidazole were placed in a flask under a drying tube, and 15 ml of N,N-dimethylformamide were added at room temperature. The reaction mixture was stirred for 30 minutes giving the following intermediate designated A.

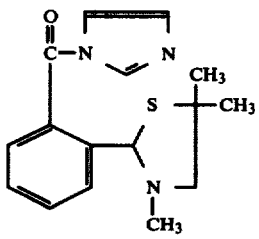

(A)

To this reaction mixture comprising the above intermediate was added 2.50 g of the azo compound designated B below.

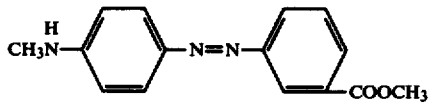

(B)

After stirring fifteen minutes, 0.50 g of a 50% oil dispersion of NaH was added in two portions. (The temperature rose slightly and foaming occurred.) The reaction mixture was stirred at room temperature for one hour and then at 60°-70° C. for two and one-half hours. After cooling to room temperature, the reaction mixture was poured into water, extracted 3x with ether and the ether extracts were washed with water, brine and dried. 200 M of the following intermediate designated C were separated from the crude reaction mixture using preparative TLC techniques.

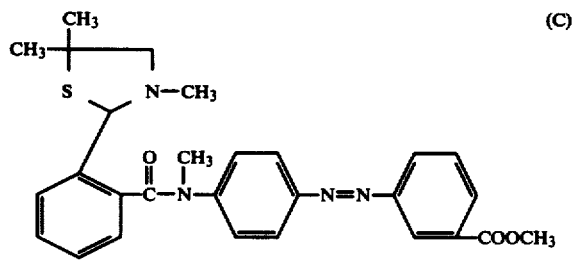

(C)

200 Mg of C was dissolved in methanol, and 7 ml of water containing potassium hydroxide was added to the methanol solution. The resulting mixture was milky, and additional methanol (about 10 ml) was added with stirring until the solution became a clear yellow. The solution was then heated to 60°-62° C. with stirring.

After TLC showed the ester hydrolysis reaction complete, the reaction mixture was placed under aspirator vacuum for 10 minutes at 60° C. and then under a vacuum pump at about 50° C. When most of the methanol had been removed, a yellow oil precipitated. The oil was dissolved in about 30 ml of water and the solution extracted 3x with ether, adjusted to pH 5 and extracted 2x with ether. The ether extracts were combined, washed with brine and dried over sodium sulfate. The title compound was purified using preparative TLC techniques.

When a sample of the title compound was dissolved in 0.5 NaOH, the resulting solution appeared stable and visually to be almost colorless. Upon the addition of silver thiosulfate, a yellow color developed within 3 seconds, and after 15-30 seconds, the solution was an intense yellow.

The azo compound B employed in the above example was prepared as follows:

3-Aminobenzoic acid (27.4 g) was placed in about 350 ml of aqueous 85% lactic acid and cooled to −10° C. Sodium nitrite (14.0 g) was dissolved in a small amount of water and added slowly to the amino acid-lactic acid solution so that the temperature remained below 0° C. After this addition was complete, stirring was continued for 30 minutes at −10° C. and then at 0° C. to +5° C. for 15 minutes. The solution was then cooled to −10° C. and N-methylaniline (30.0 g) in about 200 ml of aqueous 85% lactic acid was slowly added. A light yellow precipitate formed. The reaction solution was stirred at 0° C. for one hour and at room temperature for two hours. (The reaction mixture became red-brown). It was then heated at 70° C. for two hours and allowed to stand overnight. The reaction mixture was diluted to 2 liters with water and filtered to collect a brown solid. The brown solid comprising the crude reaction product was treated with one liter of aqueous sodium bicarbonate at room temperature and stirred. The aqueous solution was washed with ether, acidified to pH 5 and a small amount of red precipitate was isolated. A large amount of the brown crude reaction product did not dissolve so the undissolved crude product was treated with sodium bicarbonate at 80° C. After filtering, extracting the filtrate with ether and acidifying to pH 5, an orange powder was obtained. The orange powder was dissolved in 500 ml of dry methanol. HCl gas was bubbled through the methanol solution for 20 minutes, and the solution was heated to 60° C. for one hour then allowed to stand overnight. It was poured into 3.5 liters of water, and the solid collected was washed with water, stirred 3x with hot sodium bicarbonate, then dissolved in chloroform. The chloroform solution was washed with sodium bicarbonate, dried over sodium sulfate and evaporated under vacuum to give 9 g of the title compound as an orange-red oil that solidified after drying at 90° C. under vacuum.

EXAMPLE 3

Preparation of the compound having the formula

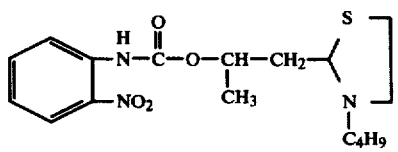

One gram of the following carbamoyl chloride-isocyanate mixture

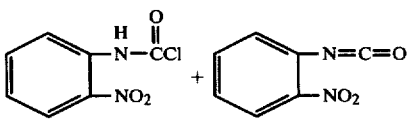

was added to approximately 20 ml of dry chloroform. To this mixture was added one gram of the thiazolidine alcohol of the formula

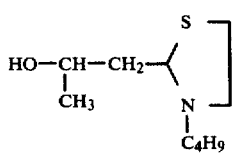

This reaction mixture was stirred at room temperature for two hours. Additional chloroform solvent was added so that any starting material present as the HCl salt would be soluble. TLC in ether was recorded. The reaction mixture was evaporated and triturated with ether. The insoluble solid was presumed to be the HCl salt of the title compound. TLC had shown a considerable amount of dark material which remained at the origin, so the solid was chromatographed on silica with chloroform as eluent. The amine and the title compound came off with the front as a mixture. TLC showed a minor amount of amine plus another colored impurity. NMR showed mostly title compound that came off as free base. The free base was soluble in ether and positions in NMR compared with those of the starting alcohol (free base).

The thiazolidine alcohol having the formula set out below was prepared as follows:

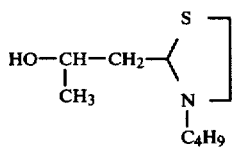

A mixture of 2-n-butylaminoethanethiol (4.5 g; 0.034 mole) and the dimer of β-hydroxy-n-butyraldehyde (3.0 g; 0.017 mole) in approximately 100 ml of benzene were refluxed under nitrogen using a Dean-Stark trap to remove water. (Water began to come over immediately and stopped after about 20 minutes.) Refluxing of the mixture was continued for one hour and then the benzene was removed by evaporation. The residue was distilled (boiling point 100° C. at 0.125 mm) to give the title compound as a colorless oil. Thiazolidine alcohol compounds form the subject matter of copending U.S. patent application Ser. No. 474,144 of Roberta R. Arbree, William J. Cumming and Frank A. Meneghini filed Mar. 9, 1983.

EXAMPLE 4

Preparation of the compound having the formula

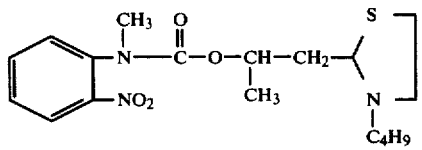

The compound of Example 3 (200 mg; 0.54 mmole) in 0.5 ml of anhydrous N,N-dimethylformamide (over 4A sieves) was added to sodium hydride (13 mg; 0.54 mmole) in N,N-dimethylformamide under nitrogen. After stirring at room temperature for 1½ hours, evolution of hydrogen had ceased. Methyl iodide (77 mg; 0.54 mmole) dissolved in N,N-dimethylformamide was added dropwise. Heat evolved. Stirring of the reaction mixture was continued at room temperature. Sodium iodide precipitated. The solution of the carbamate anion was red. As the reaction with methyliodide proceeded, the color changed to orange. The time for complete color change was about 1½ hours. Thereafter, the mixture was poured into water, extracted with ether, the ether extract washed several times with water, dried and evaporated. The yield of title compound was nearly quantitative.

EXAMPLE 5

Preparation of the compound having the formula

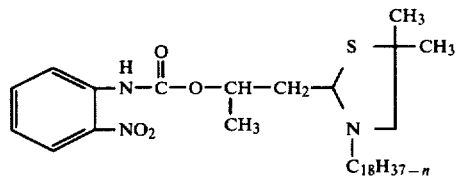

The thiazolidine alcohol of the formula,

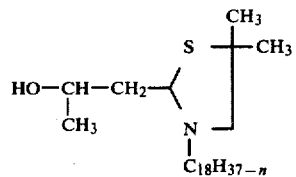

(1.85 g) was dissolved in about 25 ml dry chloroform. Solid o-nitrophenyl isocyanate was added, and the reaction mixture was stirred over the weekend. It was then evaporated, and the oil residue was dissolved in petroleum ether and extracted about five times with water. The petroleum ether layer was dried and evaporated. (NMR showed the desired product.) Some solid formed in the oil. It was insoluble in petroleum ether and was removed by dissolving the product in petroleum ether and filtering. Evaporation of the petroleum ether gave an orange oil which crystallized on standing. The crystals were slightly soluble in isopropanol. The partially crystalline oil was triturated with isopropanol, filtered and the crystals washed with isopropanol and dried to give approximately 400 mgs of the title compound as pale yellow crystals (melting range 53°-55° C.).

EXAMPLE 6

Preparation of the compound having the formula

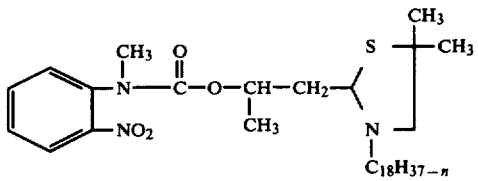

The compound of Example 6 was prepared from the compound of Example 5 (1.1 g; 1.86 mmole) according to the procedure given in Example 4 using equimolar amounts, i.e., 1.86 mmole of both sodium hydride and methyl iodide in N,N-dimethylformamide. Evaporation of the ether extract of the reaction mixture gave an orange oil. TLC showed the title compound as the major product (which changed to orange in several hours) plus a very minor amount of two yellow impurities.

EXAMPLE 7

Preparation of the compound having the formula

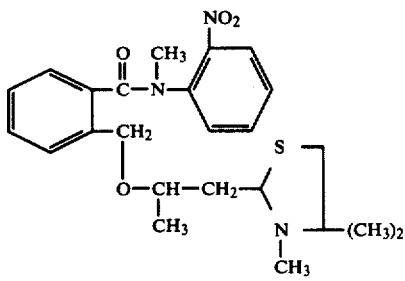

The compound of the formula

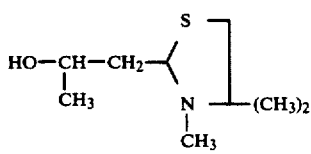

(2.3827 g; 0.0126 mol) was dissolved in 80 ml tetrahydrofuran ($Al_2O_3$ treated) and placed in a flamed out flask under argon. Potassium t-butoxide (1.695 g; 0.0151 mol) was added at room temperature and the resulting opaque, slightly orange solution was stirred for 15 minutes. Then the compound of the formula

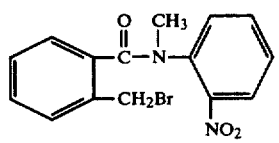

(4.395 g; 0.0126 mol) was added as a solid, and the resulting solution, which turned deep red in color, was stirred overnight. (TLC showed the desired product as well as both starting materials.) To this reaction mixture was added 3 ml of dry N,N-dimethylformamide followed by 0.7 gm of potassium t-butoxide. The solution, which became darker in color, was poured into 150 mls water/250 ml ether, shaken, separated and the ether layer washed several times with water. The ether layer was then extracted with 1N HCl (3×150 ml). The acid extracts were combined and neutralized with solid sodium bicarbonate. The cloudy aqueous solution was extracted with chloroform (2×150 ml), dried over anhydrous sodium sulfate and evaporated to dryness to give the title compound.

Purified samples of the title compound were obtained by both 1) $SiO_2$ preparative plate chromatography and three chloroform elutions and 2) medium pressure liquid chromatography using chloroform as solvent.

EXAMPLE 8

Preparation of the compound having the formula

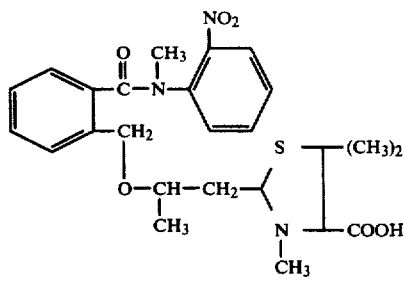

The compound of the formula,

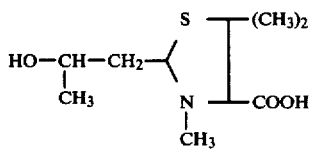

(0.1136 g; 0.487 mmole) was dissolved in approximately 3 ml tetrahydrofuran (thru $Al_2O_3$ and over sieves) and placed in a flamed out flask under argon in a 0° C. bath. To this solution was added n-butyllithium in hexane (0.61 ml/0.974 mmole) over about 5 seconds, and then the compound of the formula

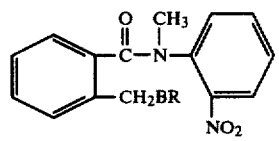

(0.170 g; 0.487 mmole) in approximately 1 ml dry tetrahydrofuran also was added over about 5 seconds. A pale yellow color was noted.

The reaction mixture was stirred at 0° C., and after 5 minutes the bath was removed. TLC after 0.5 hour at room temperature showed that product formation apparently was very slow at room temperature so the reaction mixture was heated to reflux for 2.5 hours. After cooling to room temperature, the mixture was poured into ether and filtered. The filtered material was dissolved in water and the pH adjusted to about pH 4 with 1N HCl. The precipitate that formed was removed by filtration and the filtrate extracted two times with chloroform, dried over anhydrous sodium sulfate and evaporated to dryness to yield the title compound.

As noted previously, the present invention is concerned with the formation of a color image from certain colorless image dye-providing compounds comprising a colorless precursor of a preformed image dye. In this invention, the colorless compound may be present initially in the photosensitive element in a layer or layers other than the layer containing the light-sensitive silver halide emulsion, or it may be in the light-sensitive layer itself. For example, it may be in a layer on one side of the emulsion or in two layers, one on either side of the emulsion. If desired, it may be separated from the emulsion layer by one or more spacer layers. Where the colorless compound is present in the light-sensitive layer, the compound should be inert, that is photographically innocuous in that it does not adversely affect or impair image formation. If not photographically innocuous, the compound may be modified in a manner which does not interfere with the development process in any way, but which deactivates the compound so that it does not affect adversely the light-sensitive emulsion. Rather than being disposed in the photosensitive element, the colorless compound may be initially contained in a layer associated with an image-receiving layer in processes such as diffusion transfer processes where image-receiving elements are employed.

The formation of color images according to the subject invention is applicable to the preparation of both monochromatic and multicolor images. For example, the colorless image dye-providing compounds of this invention may be employed in photographic systems utilizing multilayer photosensitive elements comprising at least two selectively sensitive silver halide emulsion strata having said colorless image dye-providing compounds associated therewith which are processed simultaneously and without separation to provide a multicolor image. In such a structure, a barrier interlayer of silver complex scavenger, e.g., silver precipitant may be used, to confine diffusion of soluble silver complex to the appropriate stratum. Also, filter layers containing, e.g., bleachable filter dyes of the type described in U.S. Pat. Nos. 4,304,833, 4,358,118 and 4,304,834 may be used to control the spectral composition of light falling on the underlying light-sensitive layer. Another useful structure for obtaining multicolor images is the screen type negative described in U.S. Pat. No. 2,968,554 or that described in U.S. Pat. No. 3,019,124.

According to one method of forming color images, both the image dyes and their colorless parent compounds comprising the colorless precursor of a preformed image dye are substantially non-diffusible from their initial position in association with the photosensitive strata. To achieve the requisite non-diffusibility, the colorless parent compound may be appropriately substituted with an immobilizing group, e.g., a long chain alkyl group and the image dye released may be a dye that is substantially non-diffusable by nature or it may be rendered non-diffusable by appropriate substitution with an immobilizing group, by including a mordant in the same layer with said image dye or by other means that would prevent the dye from diffusing from the photosensitive element.

Though the developed silver present in the photosensitive element after image formation and any remaining silver halide may be removed in a conventional manner, for example, by a bleach-fix bath, it is preferred to bleach the developed silver and to complex residual silver halide in situ. In a particularly preferred embodiment, the silver halide emulsion employed is one which upon development contains low covering power silver in the developed areas whereby the need for bleaching is obviated. In these embodiments, it will be appreciated that the silver halide developing agents, the silver halide solvents and other reagents employed should be substantially non-staining.

Rather than forming monochromatic and multicolor images non-diffusible from the photosensitive element, it will be appreciated that the image dyes provided by the colorless parent compounds may be diffusible to form the color image on a single common image-receiving layer. In this embodiment, the subsequent formation of a color transfer image preferably employs a differential in diffusibility between the colorless parent compound and the liberated dye. This differential in diffusibility may be achieved in a known manner by the appropriate selection of an immobilizing group(s), such as a long chain alkyl or alkoxy group and/or solubilizing group(s), such as, hydroxy, carboxy or sulfo groups.

In the latter embodiments, where the image dyes released are diffusible, the photosensitive layer and the image-receiving layer may be in separate elements which are brought together during processing and thereafter retained together as the final print or separated following image formation, or the photosensitive and image-receiving layers may be in the same element. For example, the image-receiving layer may be coated on a support and the photosensitive layer coated on the surface of the image-receiving layer. The processing composition may be applied to the combined negative-positive element using a spreader sheet to facilitate spreading the liquid composition in a uniform layer adjacent the surface of the photosensitive layer. The image-receiving layer carrying the color image may be separated from the overlying photosensitive layer(s), e.g., with the aid of a stripping layer, or the color image may be viewed as a reflection print by employing a light-reflecting layer between the photosensitive and image-receiving layers.

Illustrative of still other film units are those where the negative and positive components together comprise a unitary structure and are laminated and/or otherwise physically retained together at least prior to image formation. Generally, such film units comprise a plurality of layers including a negative component comprising at least one light-sensitive layer, e.g., a silver halide layer and a positive component comprising an image-receiving layer which components are laminated together or otherwise secured together in physical juxtaposition as a single structure.

Included among such structures are those adapted for forming a transfer image viewable without separation, i.e., wherein the positive component containing the transfer image need not be separated from the negative component for viewing purposes. In addition to the aforementioned layers, such film units include means for providing a reflecting layer between the image-receiving and negative components in order to mask effectively the silver image or images formed as a function of development of the silver halide layer or layers and also to provide a background for viewing the transfer image in the receiving component, without separation, by reflected light. This reflecting layer may comprise a preformed layer of a reflecting agent included in the film unit or the reflecting agent may be provided subsequent to photoexposure, e.g., by including the reflecting agent in the processing composition.

The aforementioned layers are preferably carried on a support and preferably are employed with another support positioned on the opposed surface of the layers carried by the first support so that the layers are sandwiched or confined between the support members, at least one of which is transparent to permit viewing of the final image. Such film units usually are employed in conjunction with means, such as, a rupturable container containing the requisite processing composition and adapted upon application of pressure of applying its contents to develop the exposed film unit. Film units of this type are now well known and are described, for example, in U.S. Pat. Nos. 3,415,644, 3,415,645, 3,415,646, 3,594,164 and 3,594,165.

The processing composition employed comprises an aqueous solution and usually, an aqueous alkaline solution of a silver halide developing agent and a silver halide solvent. The named ingredients may be present initially in the aqueous medium or may be present initially in the photographic film unit, for example, in the emulsion and/or image-receiving and/or spacer layers as heretofore suggested in the art. When such ingredients are present initially in the film unit, the processing composition is formed by contacting the product with a suitable aqueous medium to form a solution of these ingredients.

The alkali employed may be any of the alkaline materials heretofore employed, such as sodium or potassium hydroxide and like the developing agent and the solvent may be initially in a layer or layers of the film unit.

The silver halide solvent also may be any of the heretofore known materials, such as sodium or potassium thiosulfate, sodium thiocyanate or uracil; also the thioether-substituted uracils, pseudo-uracils and other compounds disclosed and claimed in U.S. Pat. No. 4,126,459; the 1,3-disulfonylalkanes and cycloalkanes of U.S. Pat. Nos. 3,769,014 and 3,958,992, respectively; or the alkanes containing an intralinear sulfonyl group and, e.g., an intralinear N-tosylsulfimido or N-tosylsulfoximido group as disclosed and claimed in U.S. Pat. No. 4,107,176. Also, a silver halide solvent precursor may be used such as those disclosed in U.S. Pat. No. 3,698,898 and as disclosed and claimed in copending U.S. patent application Ser. No. 382,479 filed May 27, 1982.

Examples of silver halide developing agents that may be employed are hydroquinone and substituted hydroquinones, such as tertiary butyl hydroquinone, 2,5-dimethyl hydroquinone, methoxyhydroquinone, ethoxyhydroquinone, 4'-methylphenylhydroquinone; pyrogallol and catechols, such as catechol, 4-phenyl catechol and tertiary butyl catechol; aminophenols, such as 2,4,6-diamino-orthocresol; 1,4-diaminobenzenes, such as p-phenylenediamine, 1,2,4-triaminobenzene and 4-amino-2-methyl-N,N-diethylaniline; ascorbic acid and its derivatives, such as ascorbic acid, isoascorbic acid and 5,6-isopropylidene ascorbic acid and other enediols, such as, tetramethyl reductic acid; hydroxylamines, such as N,N-di-(2-ethoxyethyl)hydroxylamine, N,N-di-(2-methoxyethyl)hydroxylamine and N,N-di-(2-methoxyethoxyethyl)hydroxylamine; and heterocyclic compounds, such as, 1-phenyl-3-pyrazolidone and 4-methyl-4-hydroxymethyl-1-phenyl-3-pyrazolidone.

Usually, though not necessarily, the processing composition includes a viscosity-increasing reagent such as a cellulosic polymer, e.g., sodium carboxymethyl cellulose, hydroxyethyl cellulose, carboxymethyl hydroxyethyl cellulose, etc.; an oxime polymer, e.g., polydiacetone acrylamide oxime; or other high molecular weight polymers.

In addition to the aforementioned ingredients, the processing composition also may contain antifoggants, preservatives and other materials as conventionally used in the art.

The processing composition may be applied to the photosensitive element, for example, by coating, dipping, spraying or by the use of a rupturable container or pod such as disclosed in U.S. Pat. No. 2,543,181, the container being positioned in the film unit so as to be capable upon rupturing of spreading its contents in a substantially uniform layer.

The photosensitive element may be any of those conventionally employed and generally comprises a silver halide emulsion carried on a base, for example, glass, paper or plastic film, such as cellulose triacetate film, polyethylene terephthalate film, polystyrene film and polyolefin films, e.g., polyethylene and polypropylene films. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

Depending upon the particular photographic system, a mordant for the dye image may be used in association with the photosensitive layers as discussed above, or a separate image-receiving element may be employed. The image-receiving layer, i.e., dyeable stratum may comprise any of the materials known in the art, such as polyvinyl alcohol, gelatin, etc., preferably containing a mordant for the transferred image dye(s). The dyeable stratum can be in the same element as the photosensitive layer or it may be in a separate element as appropriate for a given photographic process.

In diffusion transfer processes employing an aqueous alkaline processing composition, it is well known to employ an acid-reacting reagent in a layer of the film unit to lower the environmental pH following substantial dye transfer in order to increase the image stability. For example, the previously mentioned U.S. Pat. No. 3,415,644 discloses systems wherein the desired pH reduction may be effected by providing an acid-reacting layer adjacent the dyeable stratum. These layers may comprise polymers which contain acid groups, e.g., carboxylic acid and sulfonic acid groups, which are capable of forming salts with alkali metals or with organic bases; or potentially acid-yielding groups such as anhydrides or lactones. Preferably the acid polymer contains free carboxyl groups. Alternatively, the acid-reacting reagent may be in a layer adjacent to the silver halide most distant from the image-receiving layer. Another system for providing an acid-reacting reagent is disclosed in U.S. Pat. No. 3,576,625.

An inert interlayer or spacer layer may be disposed between the polymeric acid layer and the dyeable stratum in order to control or "time" the pH reduction so that it is not premature and interferes with the development process. Suitable spacer or "timing" layers for this purpose are described with particularity in U.S. Pat. Nos. 3,362,819; 3,419,389; 3,421,893; 3,455,686; and 3,575,701.

The acid-reacting layer and associated spacer layer are usually contained in the image-receiving element in systems wherein the dyeable stratum and photosensitive strata are contained on separate supports, e.g., between the support for the receiving element and the dyeable stratum. In integral film units, these layers may be associated with the dyeable stratum, e.g., on the side of the dyeable stratum opposed from the photosensitive element or, if desired, they may be associated with the photosensitive strata, as is disclosed, for example, in U.S. Pat. Nos. 3,362,821 and 3,573,043. In film units such as those described in the aforementioned U.S. Pat.

Nos. 3,594,164 and 3,594,165, they also may be contained on the spreader sheet employed to facilitate application of the processing composition.

In addition to the aforementioned layers, the film units may contain additional layers as commonly used in the art, such as a layer of antihalation dye, and/or a layer of filter dye arranged between differentially color-sensitive emulsion layers. Depending upon the particular photographic system, it may be desirable to use antihalation and filter dyes which become decolorized during photographic processing.

The following examples are given to illustrate the formation of a color image in accordance with the present invention and are not intended to be limiting.

EXAMPLE I

A photosensitive element was prepared by coating a transparent gel subcoated polyester film base with the following layers;

1. a layer of the hydrochloride salt of the compound of Example 1 coated at a coverage of 90 mgs/ft$^2$ in gelatin, said hydrochloride salt having the formula

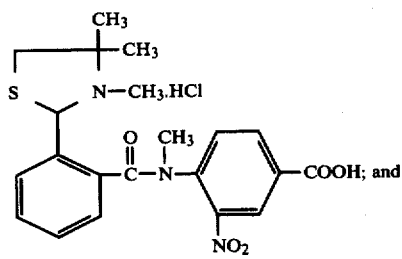

2. a gelatino silver iodobromide emulsion coated at a coverage of 50-60 mgs/ftr$^2$ silver.

The photosensitive element was exposed imagewise and processed against an image-receiving element comprising a layer of dyeable film-forming material coated on a baryta paper base at a gap of 0.0030 inch using an aqueous alkaline processing composition containing the following in % by weight:

|   |   |
|---|---|
| Carboxymethyl cellulose | 4.2 |
| Sodium hydroxide | 2.4 |
| Sodium sulfite | 2.0 |
| Sodium thiosulfate | 0.5 |
| Tetramethylreductic acid | 1.0 |
| and water to make 100% | |

After an imbibition time of three minutes in the dark, the respective elements were separated to show a positive yellow dye image.

The solution kinetics of the hydrochloride salt of the compound of Example 1 also were studied in aqueous alkaline solution in the presence and in the absence of soluble silver complex. It was found that this compound hydrolyzed with a $T\frac{1}{2}=24$ seconds in the presence of soluble silver (0.8M of NaOH, $10^{-3}$M Ag(S$_2$O$_3$)$_2$, $10^{-5}$M Ex. 1, HCl salt; 25° C.) and hydrolyzed with a $T\frac{1}{2}=115$ hours in the absence of soluble silver (1.0N aq. NaOH, $10^{-5}$M Ex. 1, HCl salt; 25° C.).

The solution kinetics of the compound of Example 2 also were studied. This compound was nearly colorless in solution and when treated with alkaline silver thiosulfate gave yellow azo dye. The azo dye formed with a $T\frac{1}{2}=32$ hours in the absence of soluble silver (0.5N aq. NaOH, $5\times10^{-5}$M Ex. 2; 25° C.) and with a $T\frac{1}{2}=11$ seconds in the presence of soluble silver (0.5N aq. NaOH, $10^{-3}$M Ag(S$_2$O$_3$)$_2$, $5\times10^{-5}$M; 25° C.). A plot of the optical density versus time for azo dye formation gave an "S" shaped curve, typical of an $A\overset{T\frac{1}{2}a}{\to}B\overset{T\frac{1}{2}b}{\to}C$ reaction, from which values of $T\frac{1}{2}^a=1$ to 3 seconds and $T\frac{1}{2}^b=10$ seconds could be estimated.

EXAMPLE II

Two photosensitive elements were prepared by coating a gelatin subcoated polyethylene terephthalate film base with a gelatino silver iodobromide emulsion. One of said photosensitive elements was coated at a coverage of 20 mgs/ft$^2$ of silver, and the other of said elements was coated at a coverage of 40 mgs/ft$^2$ of silver.

A second element containing a compound of the present invention was prepared employing a component similar to that described in U.S. Pat. No. 3,647,437 (column 66, lines 46 to 59) which comprised a transparent polyethylene terephthalate film base carrying the following layers.

(1) a polymeric acid layer
(2) a polymeric spacer (timing) layer
(3) a polymeric image-receiving layer.

To form said second element, the above component was coated (over the image-receiving layer) with (a) 100 mgs/ft$^2$ of poly-4-vinylpyridine containing 100 mgs/ft$^2$ of the colorless image dye-providing compound of Example 3 (or 100 mgs/ft$^2$ of the colorless image dye-providing compound of Example 4) and (b) 30 mgs/ft$^2$ of gelatin containing succindialdehyde hardener.

The photosensitive elements were given an exposure through a stepwedge to white light of 2 mcs and superposed with said second elements. A layer of an aqueous alkaline processing composition approximately 0.0020 inch thick was distributed between said elements by passing the film units between a pair of pressure-applying rolls in the dark. The processing composition comprised the following ingredients.

|   |   |
|---|---|
| Water | 100 cc |
| Potassium hydroxide | 5 g |
| Sodium sulfite | 2 g |
| 6-methylthiomethyl-2,4-dihydroxy-pyrimidine | 1.5 g |
| Tetramethyl reductic acid | 6 g |
| Hydroxyethyl cellulose | 3 g |
| Titanium dioxide | 50 g |

After applying said processing composition the film units were maintained intact to provide an integral negative-positive reflection print, and at recorded time intervals, the maximum and minimum reflection densities were measured for the positive yellow images. The densities measured at given times are set forth in Table I below.

TABLE I

| Cpd of Ex. 3 (20 mgs/ft$^2$ Ag) | | Cpd of Ex. 3 (40 mgs/ft$^2$ Ag) | | Cpd of Ex. 4 (40 mgs/ft$^2$ Ag) | |
|---|---|---|---|---|---|
| Time | Dmax/Dmin | Time | Dmax/Dmin | Time | Dmax/Dmin |
| 10 min | 0.37/0.25 | 10 min | — | 10 min | 0.38/0.33 |
| 20 min | 0.40/0.27 | 20 min | 0.44/0.24 | — | — |
| 30 min | 0.40/0.27 | — | — | — | — |
| 40 min | 0.41/0.27 | 75 min | 0.49/0.27 | 40 min | 0.50/0.32 |
| 2.5 hrs | 0.47/0.28 | 3.5 hrs | 0.52/0.29 | 2.5 hrs | 0.95/0.52 |
| 18 hrs | 0.60/0.54 | 18 hrs | 0.64/0.56 | — | — |

EXAMPLE III

A photosensitive element was prepared by coating a gelatin subcoated polyethylene terephthalate film base with a gelatino silver iodobromide emulsion at a coverage of 40 mgs/ft² of silver.

A second element was prepared in the same manner described in Example II above except that the coating (a) contained 150 mgs/ft² of the compound of Example 6 in 100 mgs/ft² of poly-4-vinylpyridine.

The unexposed photosensitive element was superposed with said second element and one-half of the resulting sandwich was processed with a layer (0.0020 inch thick) of an aqueous 5% sodium hydroxide solution containing 3% of hydroxyethyl cellulose and the other half of the sandwich was processed with a layer (0.0020 inch thick) of an aqueous 5% sodium hydroxide solution containing 1.5% of 6-methylthiomethyl-2,4-dihydroxypyrimidine silver halide solvent and 3% of hydroxyethyl cellulose. The optical transmission densities were measured at given time intervals for the two halves of the sandwich and showed the formation of dye from the colorless precursor. The results obtained are set forth in Table II below.

TABLE II

| Time (min.) | Optical Transmission Density | |
|---|---|---|
| | Without Solvent | With Solvent |
| 10 | 0.27 | 0.27 |
| 27 | 0.24 | 0.32 |
| 39 | 0.25 | 0.55 |
| 57 | 0.28 | 0.73 |

EXAMPLE IV

A photosensitive element was prepared by coating a transparent polyethylene terephthalate film base with the following layers.

(1) a layer containing 50 mgs/ft² of poly-4-vinylpyridine and 150 mgs/ft² of the compound of Example 5, (2) a layer of gelatin coated at a coverage of 100 mgs/ft², (3) a gelatino silver iodobromide emulsion layer coated at a coverage of 60 mgs/ft² of silver, and (4) a layer of gelatin containing succindialdehyde.

To show the formation of dye in the presence of silver halide complex, the unexposed photosensitive element was superposed with a second element similar to that described in U.S. Pat. No. 3,647,437 (column 66, lines 46 to 59) which comprised a transparent polyethylene terephthalate film base carrying the following layers:

(1) a polymeric acid layer
(2) a polymeric spacer (timing) layer
(3) a polymeric image-receiving layer.

The superposed elements were processed in the same manner using the same two processing compositions as in Example III above to show the formation of dye from the colorless precursor in the presence of silver halide complex. The optical transmission densities that were measured at given time intervals are set forth in Table III below.

TABLE III

| Time | Optical Transmission Density | |
|---|---|---|
| | Without Solvent | With Solvent |
| 1 min. | 0.13 | 0.14 |
| 3 min. | 0.14 | 0.15 |

TABLE III-continued

| Time | Optical Transmission Density | |
|---|---|---|
| | Without Solvent | With Solvent |
| 10 min. | 0.18 | 0.20 |
| 1 hr | 0.17 | 0.26 |
| 1 day | 0.26 | 0.36 |
| 7 day | 0.45 | 0.60 |

EXAMPLE V

A photosensitive element was prepared by coating a transparent polyethylene terephthalate film base with the following layers.

(1) A layer of gelatin containing the compound of Example 7, (2) a gelatino silver iodobromide emulsion layer coated at a coverage of 20 mgs/ft² of silver, and (3) a layer of gelatin containing succindialdehyde.

The unexposed photosensitive element was superposed with a second element comprising a transparent polyethylene terephthalate film base coated with the following layers.

(1) as a polymeric acid layer, a mixture of about 9 parts of a partial butyl ester of polyethylene/maleic anhydride copolymer and 1 part of polyvinyl butyral coated at a coverage of about 2,500 mgs/ft²;

(2) a timing layer containing a 14:1 ratio of a 60-30-4-6 tetrapolymer of butylacrylate, diacetone acrylamide, styrene and methacrylic acid and polyvinyl alcohol at a coverage of 500 mgs/ft²; and (3) a blend of 3 parts by weight of a 2:1 mixture, by weight, of polyvinyl alcohol and poly-4-vinylpyridine and 1 part by weight of a graft copolymer of 4-vinylpyridine and vinylbenzyltrimethylammoniumchloride grafted on hydroxyethyl cellulose in a weight ratio of 2.2/1/2.2, respectively, coated at a coverage of 300 mgs/ft² to provide an image-receiving layer.

The resulting sandwich was processed by applying a layer (0.0020 inch thick) of an aqueous 7% sodium hydroxide solution containing 2.5% of carboxymethyl hydroxyethyl cellulose to one-half of the sandwich and applying to the other half, a layer (0.0020 inch thick) of an aqueous 7% sodium hydroxide solution containing 1.5% of 6-methylthiomethyl-2,4-dihydroxypyrimidine silver halide solvent, 0.009% of 2-thiouracil and 2.5% of carboxymethyl hydroxyethyl cellulose. After 10 minutes, the optical transmission density measured for the half processed without silver halide solvent was 0.16 and the density measured for the half processed with silver halide solvent was 0.24.

An identical photosensitive element was processed in the same manner described above except that a transparent polyethylene terephthalate sheet was employed as the second element. The optical transmission densities measured for the no silver solvent-silver solvent portions of the sandwich like those above, also showed formation of dye from the colorless precursor in the presence of silver halide complex and were 0.35 and 0.73, respectively.

EXAMPLE VI

A photosensitive element was prepared by coating a transparent polyethylene terephthalate film base with the following layers.

(1) a layer containing 55 mgs/ft² of cellulose acetate hydrogen phthalate and 110 mgs/ft² of the compound of Example 8, (2) a gelatino silver iodobromide emulsion layer coated at a coverage of 25 mgs/ft² of silver and containing 30 mgs/ft² of 4'-methylphenylhydroquinone, and (3) a layer of gelatin coated at a coverage of 30 mgs/ft².

A second element was prepared by coating a transparent polyethylene terephthalate film base with the following layers.

(1) as a polymeric acid layer, a mixture of about 9 parts of a partial butyl ester of polyethylene/maleic anhydride copolymer and 1 part of polyvinyl butyral coated at a coverage of about 2,500 mgs/ft²;

(2) a timing layer containing a 14:1 ratio of a 60-30-4-6 tetrapolymer of butylacrylate, diacetone acrylamide, styrene and methacrylic acid and polyvinyl alcohol at a coverage of 500 mgs/ft²;

(3) a blend of 3 parts by weight of a 2:1 mixture, by weight, of polyvinyl alcohol and poly-4-vinylpyridine and 1 part by weight of a graft copolymer of 4-vinylpyridine and vinylbenzyltrimethylammoniumchloride grafted on hydroxyethyl cellulose in a weight ratio of 2.2/1/2.2, respectively, coated at a coverage of 300 mgs/ft² to provide an image-receiving layer.

One-half of the photosensitive element was exposed to white light, the other half being left unexposed. The photosensitive element was superposed with said second element and the sandwich was processed by applying a layer of processing composition 0.0010 thick containing the following ingredients.

| Water | 100 cc |
| --- | --- |
| Potassium hydroxide | 14 g |
| 6-butylthiomethyl-2,4-dihydroxypyrimidine | 3 g |
| Carboxymethyl hydroxyethyl cellulose | 2.5 g |

After 5 minutes in the dark, the optical transmission densities measured for the exposed and unexposed portions of the film unit were 0.27 and 0.57 respectively.

It will be appreciated that the photographic systems of the present invention for providing a color image may be used with film structures other than those illustrated.

Since certain changes may be made in the herein-defined subject matter without departing from the scope of the invention herein involved, it is intended that all matter contained in the above description should be interpreted as illustrative and not in a limiting sense.

What is claimed is:

1. A photographic color process which provides a dye image, said process comprising photoexposing a photosensitive element containing a silver halide emulsion, said silver halide emulsion having associated therewith a colorless precursor of a preformed image dye; developing said exposed silver halide emulsion to form an image in developed silver and an imagewise distribution of silver ion and/or soluble silver complex in the partially developed and undeveloped areas of said emulsion; and forming as a function of said development a color image on dye from said colorless precursor, said colorless precursor of a preformed dye being substituted with a moiety comprising a 1,3-sulfur-nitrogen group that maintains said precursor in its colorless form until said 1,3-sulfur-nitrogen group undergoes cleavage in the presence of said silver ions and/or soluble silver complex formed as a function of development, said 1,3-sulfur-nitrogen group possessing a carbon atom in the 2-position intermediate said sulfur and nitrogen atoms.

2. A process as defined in claim 1 wherein said image dye is substantially non-diffusible from the layer in which it is positioned during said photoexposure.

3. A process as defined in claim 1 wherein said colorless precursor is substantially non-diffusible from the layer in which it is positioned during said photoexposure.

4. A process as defined in claim 3 wherein said colorless precursor is positioned in said silver halide emulsion during photoexposure.

5. A process as defined in claim 1 wherein said image dye provided by said colorless precursor is diffusible, said process including the step of transferring said diffusible image dye to an image-receiving layer in superposed relationship with said silver halide emulsion.

6. A process as defined in claim 5 wherein a light-reflecting layer is provided between said silver halide emulsion and said image-receiving layer, whereby said dye image may be viewed against said light-reflecting layer, said light-reflecting layer being effective to mask said developed silver halide emulsion from one viewing said dye image.

7. A process as defined in claim 1 wherein said silver halide emulsion is a negative working silver halide emulsion whereby a positive color image is formed as a function of said development.

8. A photographic product comprising a photosensitive element comprising a plurality of layers including a support; a silver halide emulsion in a layer on said support; and in a layer on the same side of said support as said silver halide emulsion, a colorless precursor of a preformed image dye substituted with a moiety comprising a 1,3-sulfur-nitrogen group that undergoes cleavage in the presence of silver ions and/or soluble silver complex, said moiety maintaining said precursor in its colorless form until said 1,3-sulfur-nitrogen group undergoes said cleavage, said 1,3-sulfur-nitrogen group possessing a carbon atom in the 2-position intermediate said sulfur and nitrogen atoms.

9. A photographic product as defined in claim 8 wherein said colorless precursor is non-diffusible in aqueous alkaline solution.

10. A photographic product as defined in claim 8 wherein said image dye provided by said colorless precursor is non-diffusible in aqueous alkaline solution.

11. A photographic product as defined in claim 8 wherein said image dye provided by said colorless precursor is diffusable in aqueous alkaline solution and said product includes an image-receiving layer so positioned as to be capable of receiving by diffusion said imagewise distribution of said diffusible dye.

12. A photographic product as defined in claim 11 which additionally includes means for applying an aqueous processing composition to provide an aqueous alkaline solution of a silver halide developing and a silver halide solvent.

13. A photographic product as defined in claim 11 which includes a light-reflecting layer between said silver halide emulsion and said image-receiving layer, whereby said dye image formed by said imagewise distribution of diffusible dye may be viewed by reflection, said light-reflecting layer being effective to mask said developed silver halide emulsion from one viewing said dye image.

14. A photographic product as defined in claim 8 wherein said colorless precursor is positioned in said silver halide emulsion.

15. A photographic product as defined in claim 8 which includes a silver halide developing agent in said silver halide emulsion layer.

16. A photographic product as defined in claim 15 which includes a silver halide solvent in a layer on the same side of the support as said silver halide emulsion.

17. A photographic product as defined in claim 8 wherein said silver halide emulsion is a negative working emulsion.

18. A photographic product as defined in claim 8 which additionally includes an acid-reacting layer.

* * * * *